(12) United States Patent
Arni

(10) Patent No.: US 8,491,302 B2
(45) Date of Patent: Jul. 23, 2013

(54) DENTAL IMPLANT

(76) Inventor: Uri Arni, Beer Yaacov (IL)

(*) Notice: Subject to any disclaimer, the term of this patent is extended or adjusted under 35 U.S.C. 154(b) by 575 days.

(21) Appl. No.: 12/293,787

(22) PCT Filed: Mar. 21, 2007

(86) PCT No.: PCT/IL2007/000369
§ 371 (c)(1),
(2), (4) Date: Aug. 6, 2010

(87) PCT Pub. No.: WO2007/107995
PCT Pub. Date: Sep. 27, 2007

(65) Prior Publication Data
US 2011/0045437 A1    Feb. 24, 2011

Related U.S. Application Data

(60) Provisional application No. 60/784,833, filed on Mar. 21, 2006.

(51) Int. Cl.
*A61C 8/00*      (2006.01)
*A61C 13/225*    (2006.01)

(52) U.S. Cl.
USPC .......................................... 433/173; 433/172

(58) Field of Classification Search
USPC ............... 433/172–176, 201.1; 606/264–272, 606/275, 300–321; 411/412, 413, 307
See application file for complete search history.

(56) References Cited

U.S. PATENT DOCUMENTS

| | | | |
|---|---|---|---|
| 5,427,527 A | 6/1995 | Niznick et al. | |
| 5,816,812 A | 10/1998 | Kownacki et al. | |
| 5,964,768 A | 10/1999 | Huebner | |
| 6,030,162 A | 2/2000 | Huebner | |
| 6,547,564 B1 | 4/2003 | Hansson | |
| 2004/0006346 A1 | 1/2004 | Holmen et al. | |
| 2004/0063071 A1 | 4/2004 | Schroering | |
| 2004/0219488 A1 | 11/2004 | Choi et al. | |
| 2005/0131413 A1* | 6/2005 | O'Driscoll et al. | 606/73 |
| 2005/0276676 A1 | 12/2005 | Mardinger et al. | |
| 2007/0233122 A1* | 10/2007 | Denis et al. | 606/73 |

FOREIGN PATENT DOCUMENTS

| | | |
|---|---|---|
| EP | 0 412 845 | 2/1991 |
| EP | 0 705 572 | 4/1996 |
| EP | 0 705 572 A2 | 4/1996 |

OTHER PUBLICATIONS

Office Action for Israeli Patent Application No. 194200 mailed on Oct. 9, 2011; 3 pages.

* cited by examiner

*Primary Examiner* — Yogesh Patel
(74) *Attorney, Agent, or Firm* — Shichrur & Co.

(57) ABSTRACT

A dental implant with a coarsely threaded portion suitable for nesting within the cortical bone, and a finely threaded portion suitable for nesting within the cancellous bone. A primary thread with a constant pitch and a constant major diameter, runs along both the finely threaded portion and the coarsely threaded portion, and has a large thread height in the coarsely threaded portion, and a small thread height in the finely threaded portion. At least one secondary thread, having the constant pitch and the small thread height, runs along the finely threaded portion at an offset from the primary thread.

13 Claims, 6 Drawing Sheets

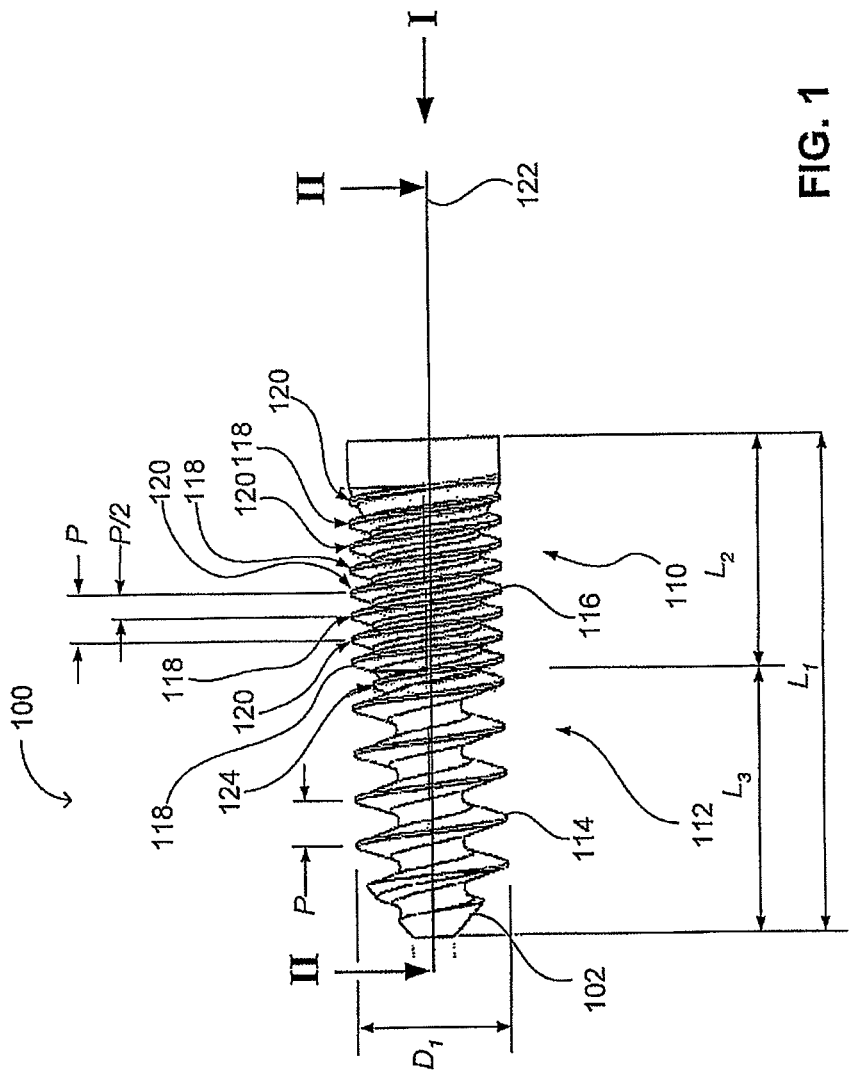
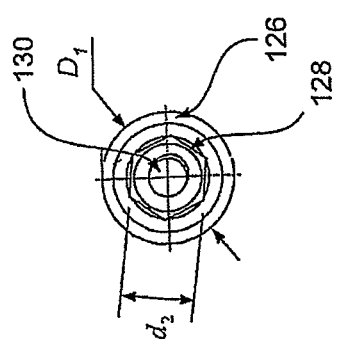
FIG. 1
FIG. 2

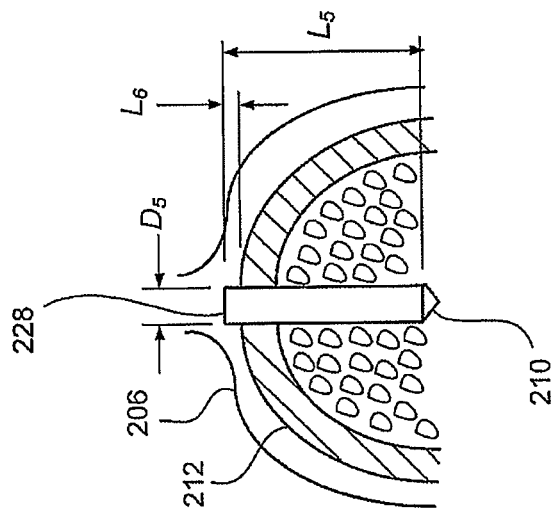
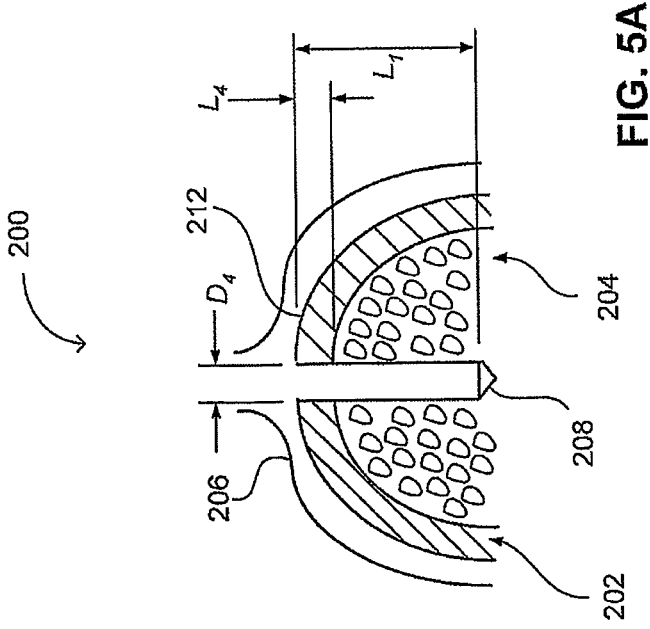

DENTAL IMPLANT

This application is a National Stage Application of PCT/IL2007/000369, filed 21 Mar. 2007, which claims benefit of U.S. application Ser. No. 60/784,833, filed 21 Mar. 2006 and which applications are incorporated herein by reference. To the extent appropriate, a claim of priority is made to each of the above disclosed applications.

FIELD OF THE INVENTION

The disclosed technique relates to medical devices in general, and to methods and systems for performing a dental implant, in particular.

BACKGROUND OF THE INVENTION

A tooth can be implanted by inserting a dental implant into the jawbone (i.e., either the mandible or the maxilla), and by attaching a substitute or an artificial tooth to the dental implant. Generally, the dental implant is in form of an externally threaded screw, which is screwed into a pre-drilled bore of the jawbone, at an appropriate diameter. A major problem with dental implants is the dislodging of the dental implant, after a certain period of use, due to the forces which act on the dental implant during mastication.

Screw profiles and anchoring means directed to increase the bonding forces between the jawbone, and the dental implant, and to increase the life of the dental implant are known in the art. One such anchoring means utilizes grooves and holes in the body of the dental implant, to allow the osseous cells to grow into the grooves and the holes. Other anchoring means utilize screw threads of different pitches along the length of the anchoring means.

A major cause of dislodging of the anchoring means is insufficient bonding area. This problem is especially pronounced in the cancellous bone of the mandible and the maxilla, which is porous and therefore much weaker than the compact cortical bone. The cancellous bone is located beneath the cortical bone, and very often the anchoring forces which act between the dental implant and the cancellous bone are very small, thereby lending the bottom portion of the dental implant, which enters into the cancellous bone, literally useless.

U.S. Pat. No. 6,547,564 issued to Hansson, and entitled "Bone Implant Having Circumferentially Oriented Roughness", is directed to a self tapping endosseous screw-type dental implant. The dental implant has an apical end, an intermediate section, and a coronal end. The apical end is presented by a first conical section. The coronal end is presented by a second conical section. The intermediate section is of a constant diameter, and extends from the apical end to the coronal end. The outer surface of the dental implant is provided with a screw threading which is divided into a coronal section and an apical section. The coronal section is positioned on the intermediate section. The apical section bridges the intermediate section and the first conical section.

The screw thread in the coronal section is in form of microthreads, having a height which is no greater than 0.2 mm, aligned parallel with one another at an inclined angle to the rotational axis. The screw thread in the apical section is in form of a macrothread, having a height greater than 0.2 mm, and in case of more than one macrothread, all macrothreads are also aligned parallel with one another, at an angle inclined to the rotational axis. The pitch of the screw thread of the apical section is the same as that of the coronal section. The quantity of the macrothreads in the apical section is less than that of the microthreads in the coronal section.

US Patent Application Publication No. 2005/0276676 A1, to Mardinger et al., and entitled "Orthopedic or Dental Device", is directed to a dental device having a screw thread whose feature is variable along the length of the dental device. These features include the spacing between adjacent turns of the thread, the height of the thread, and the thickness of the thread. The feature can vary either continuously, or in an abrupt manner. A segment of the screw thread having widely spaced turns is meant to be inserted into a cancellous bone tissue, while another segment of the screw thread having narrowly spaced turns is meant to be inserted into compact bone tissue.

U.S. Pat. No. 6,030,162 issued to Huebner and entitled "Axial Tension Screw" is directed to a screw having a leading section, an intermediate section, a trailing section, and a self drilling tip. The screw thread of the leading section has a constant pitch. The screw thread of the trailing section has a constant but smaller pitch, and the screw thread of the intermediate section has a variable pitch connecting the leading section and the trailing section.

U.S. Pat. No. 5,427,527 issued to Niznick et al., and entitled "Dental Implant Method of Installation", is directed to a cylindrical threaded implant. The implant has an angled abutment at a top portion thereof. The threads of the implant are interrupted by a plurality of closely spaced longitudinal channels, to provide a serrated appearance.

SUMMARY OF THE INVENTION

It is an object of the disclosed technique to provide a novel dental implant for attaching a tooth to a jawbone, and a method for implanting the dental implant in the jawbone.

In accordance with the disclosed technique, there is thus provided a dental implant for implanting a tooth in a jawbone. The dental implant includes a coarsely threaded portion suitable for nesting within the entire width of the cortical bone of the jawbone, and within a small portion of the cancellous bone of the jawbone. The dental implant further includes a finely threaded portion suitable for nesting within the cancellous bone of the jawbone. A primary thread runs along both the finely threaded portion and the coarsely threaded portion. The primary thread has a constant pitch and a constant major diameter, a large thread height in the coarsely threaded portion, and a small thread height in the finely threaded portion.

The small thread height is substantially greater than the height of a microthread, and the large thread height is larger than the small thread height. The primary thread has a primary thread angle more acute than 45 degrees. The dental implant further includes at least one secondary thread having the constant pitch and the small thread height, which runs along the finely threaded portion, at an offset from the primary thread. The at least one secondary thread has a secondary thread angle more acute than 45 degrees.

According to another aspect of the disclosed technique, there is thus provided a method for implanting a dental implant in a jawbone of a patient. The method includes the procedures of drilling a first bore in the jawbone, inserting a guide pin into the first bore, drilling a second bore through the cortical bone, removing the guide pin from the jawbone, and screwing the dental implant into the jawbone.

The first bore passes through a cortical bone and a cancellous bone of the jawbone. The first bore has a first diameter. The first diameter matches a small minor diameter of a coarsely threaded dental implant distal portion of the dental implant. A bore length of the first bore matches a dental implant length of the dental implant. A bore distal part of the first bore is dedicated for tapping of the dental implant distal portion in the cancellous bone.

The second bore partially penetrates the cancellous bone, and it is drilled by employing a guided drill bit which employs the guide pin as a drilling guide. The second bore has a second diameter larger than the first diameter. The second diameter matches a large minor diameter of a finely threaded dental implant proximal portion of the dental implant. The second bore is dedicated for tapping the dental implant proximal portion.

BRIEF DESCRIPTION OF THE DRAWINGS

The disclosed technique will be understood and appreciated more fully from the following detailed description taken in conjunction with the drawings in which:

FIG. 1 is a schematic illustration of a dental implant, constructed and operative according to an embodiment of the disclosed technique;

FIG. 2 is a schematic illustration of a side view (view I) of the dental implant of FIG. 1;

FIG. 5A is a schematic illustration of a portion of a mandible in which a bore is drilled, for tapping therein the dental implant of FIG. 1;

FIG. 5B is a schematic illustration of the mandible of FIG. 5A, which includes a guide pin inserted into the bore illustrated in FIG. 5A;

DETAILED DESCRIPTION OF THE EMBODIMENTS

The disclosed technique overcomes the disadvantages of the prior art by providing a dental implant which includes a coarsely threaded portion and a finely threaded portion, on the dental implant. The dental implant includes a primary thread, and one or more secondary threads. The primary thread runs along the finely threaded portion and the coarsely threaded portion. The primary thread has a constant pitch and a constant major diameter. A minor diameter of the primary thread in the coarsely threaded portion is smaller than that of each of the secondary threads. Accordingly, the thread height of the primary thread in the coarsely threaded portion is larger than the thread height of either of the secondary threads or of the primary thread, in the finely threaded portion.

The pitch of each of the secondary threads is the same as that of the primary thread. Each of the secondary threads runs along the finely threaded portion, at an offset from the primary thread, equal to the value of the pitch of the primary thread, divided by the quantity of the secondary threads, plus one.

Preferably, a thread angle of each of the secondary threads is the same as that of the primary thread. The primary thread is dedicated for being tapped in both the cortical bone and the cancellous bone (i.e., a spongy region of the jawbone), and each of the secondary threads is dedicated for being tapped mainly in the cortical bone. The screw strength of a screw is proportional to the screw thread stress area of the screw. Since the minor diameter of the primary thread is smaller than that of each of the secondary threads, the screw strength of the coarsely threaded portion of the dental implant according to the disclosed technique, is greater than that of a dental implant in which the minor diameter of the coarsely threaded portion, is the same as that of the finely threaded portion. The term "thread height" herein below, refers to half the difference between a major diameter of a screw thread, and a minor diameter of the screw thread.

Figure 4:
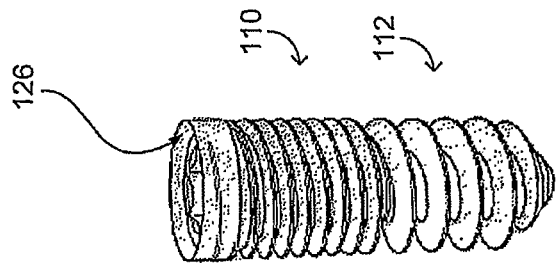
FIG. 4 is a schematic illustration of a perspective view of the dental implant of FIG. 1.
Figure 3:
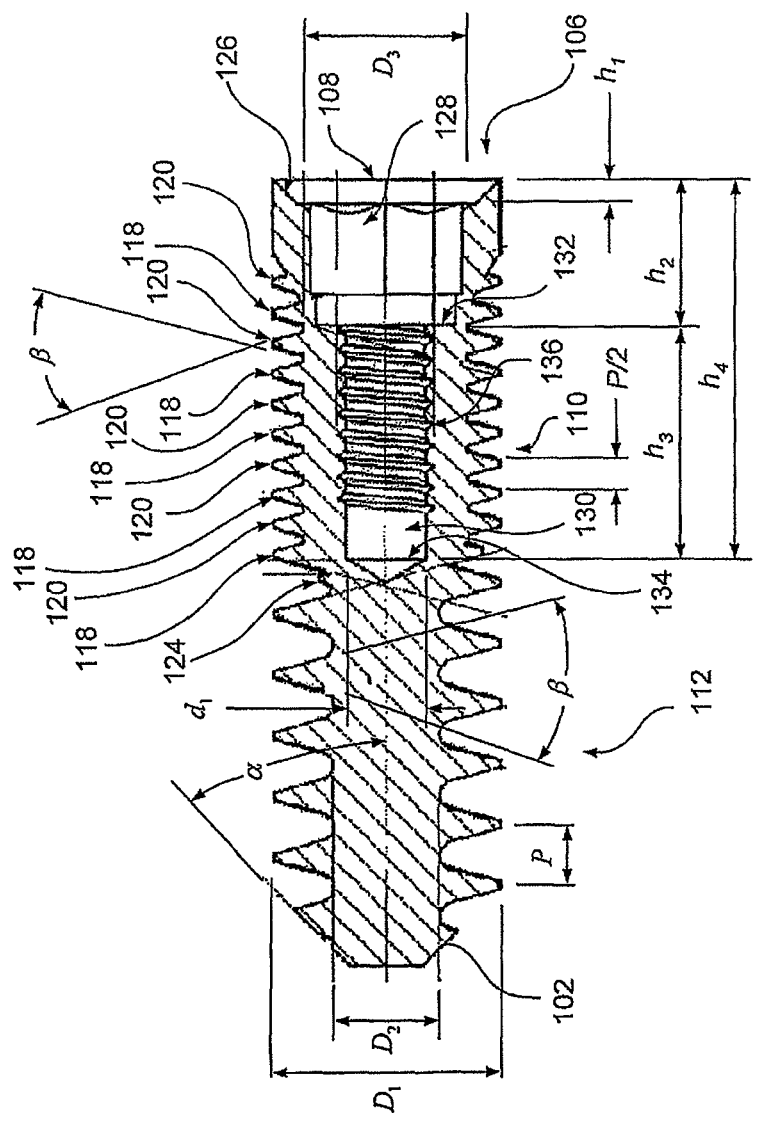
FIG. 3 is a schematic illustration of a longitudinal section (section II-II) of the dental implant of FIG. 1.

Reference is now made to FIGS. 1, 2, 3, and 4. FIG. 1 is a schematic illustration of a dental implant generally referenced 100, constructed and operative according to an embodiment of the disclosed technique. FIG. 2 is a schematic illustration of a side view (view I) of the dental implant of FIG. 1. FIG. 3 is a schematic illustration of a longitudinal section (section II-II) of the dental implant of FIG. 1. FIG. 4 is a schematic illustration of a perspective view of the dental implant of FIG. 1.

With reference to FIGS. 1 and 3, dental implant 100 includes a finely threaded portion 110 (i.e., finely threaded dental implant proximal portion), and a coarsely threaded portion 112 (i.e., coarsely threaded dental implant distal portion). Finely threaded portion 110 is proximal to the outer part of the jawbone, where an artificial tooth (not shown) is to be coupled to. Coarsely threaded portion 112 is at a distal end of dental implant 100. Finely threaded portion 110 is between 5 to 6.5 mm long, and coarsely threaded portion 112 is between 6.5 to 8 mm long, correspondingly, such that dental implant 100 is approximately 13 mm long.

Coarsely threaded portion 112 includes a distal end 102, which is an optional feature in form of a truncated cone tapering at an angle of α, in order to facilitate self tapping of dental implant 100 into a jawbone (not shown) of a patient (not shown). The screw thread along coarsely threaded portion 112 continues up to distal end 102. Distal end 102 is particularly short in order to avoid reduction of bonding area when dental implant 100 is subject to dislodging forces, and can be entirely eliminated, if such self tapping facilitation is redundant.

Finely threaded portion 110 has a minor diameter $D_3$ (FIG. 3), which is greater than a minor diameter $D_2$ of coarsely threaded portion 112. A proximal end 106 of dental implant 100 includes a proximal surface 108, a countersink 126, a hexagonal socket 128, and a bore 130. Bore 130 includes a top surface 132 and a bottom surface 134. Countersink 126 is located at proximal surface 108, and on the top of hexagonal socket 128. A portion of bore 130 includes an internal thread 136 running from top surface 132 toward bottom surface 134. Bore 130 is generally disposed within finely threaded portion 110.

A depth of countersink 126 is referenced $h_1$. A socket depth of hexagonal socket 128 from proximal surface 108, is referenced $h_2$. An opening between every two internal surfaces of hexagonal socket 128, is referenced $d_2$ (FIG. 2). A depth of bore 130 from top surface 132 to bottom surface 134 is referenced $h_3$. A distance between proximal surface 108 to bottom surface 134 is referenced $h_4$. A diameter of bore 130 is referenced $d_1$.

A dental surgeon (not shown) screws dental implant 100 into the jawbone, by employing a mounting device (e.g., an Allen wrench—not shown), which fits hexagonal socket 128. A major diameter (not shown) of internal thread 136 is such that a wall thickness (not shown) between internal thread 136 and minor diameter $D_3$, is of such a value that the strength of dental implant 100 is not compromised. Alternatively, bore 130 can extend within coarsely threaded portion 112, if the diameter (not shown) of bore 130 and is smaller than minor diameter $D_2$ such that wall thickness (not shown) between bore 130 (or internal thread 136) and minor diameter $D_2$, is of such a value that the strength of dental implant 100 is not compromised. It is noted that the screw thread of finely threaded portion 110 can extend up to proximal surface 108.

After implanting dental implant 100 within the jawbone, the dental surgeon screws a flat head screw (not shown), in internal thread 136, and sutures the wound in the jawbone. The head of the flat head screw fits countersink 126, thereby positively sealing hexagonal socket 128 during the healing period. When the jawbone grows, the dental surgeon removes the flat head screw, and mounts an artificial tooth (not shown) on proximal end 106. The dental surgeon can mount the artificial tooth on dental implant 100, by screwing an external threaded portion of the artificial tooth, into internal thread 136. Alternatively, the dental surgeon can mount the artificial tooth on dental implant 100, by applying an adhesive between the artificial tooth and hexagonal socket 128 or bore 130.

The mounting device may further include a pin that enters bores 130, for imparting rigidity between the mounting device and dental implant 100. In order to prevent contamination, the manufacturer of dental implant 100, can pack dental implant 100 together with the mounting device, in an sterilized enclosure. In this case, throughout the operation, the dental surgeon comes in contact only with the mounting device, and discards the mounting device after implanting dental implant 100 in the jawbone. In this case, hand contact with dental implant 100 is prevented.

Dental implant 100 is of a length $L_1$ and includes finely threaded portion 110 of a length $L_2$ and coarsely threaded portion 112 of a length $L_3$. Dental implant 100 further includes a primary thread 114 and one or more secondary threads 116. Primary thread 114 runs seamlessly along the entire length of dental implant 100, namely—along both finely threaded portion 110 and coarsely threaded portion 112. Primary thread 114 has a constant pitch P, and a major diameter $D_1$. The value of major diameter $D_1$ is between 3.75 and 4.6 mm. The value of constant pitch P is between 1 and 1.3 mm. Primary thread 114 has a large thread height (not shown) in coarsely threaded portion 112, and a small thread height (not shown) in finely threaded portion 110, wherein the large thread height is larger than the small thread height. The value of the small thread height is between 0.4 and 0.7 mm. The value of the large thread height is between 1 and 1.4 mm.

The large thread height defines a small minor diameter $D_2$ respective of primary thread 114. The small thread height defines a large minor diameter $D_3$ respective of each of secondary threads 116, wherein $$D_3 > D_2 \quad (1)$$

It is noted that the greater the difference between major diameter $D_1$ and each of minor diameters $D_2$ and $D_3$, respectively, the greater is the thread height and the greater is the contact surface between dental implant 100 and the jawbone. This substantially large contact surface, has a significant role in resisting the tensile forces and the moments, which act on dental implant 100 especially during mastication. Therefore, this contact surface should be as large as possible.

In order to avoid moments and tensile forces which can damage dental implant 100 during the screwing operation within the jawbone, the pitch of each of secondary threads 116, substantially equals to pitch P of primary thread 114. Each of secondary threads 116 runs in parallel to the primary thread 114, along finely threaded portion 110, at an offset. This offset equals to P/(n+1), where n=1, 2, 3 . . . N is the quantity of the secondary threads 116, which are manufactured in finely threaded portion 110. In case there is only one secondary thread 116, n=1, and the offset equals to half of the pitch P.

Preferably, a thread angle β of primary thread 114 (i.e., primary thread angle) is substantially the same as that of each of secondary threads 116 (i.e., secondary thread angle), although the primary thread angle and the secondary thread angle can be different. Each of the primary thread angle and the secondary thread angle is an acute angle of less than 45 degrees, and preferably 30 degrees. Primary thread 114 is represented by a plurality of crests 118. Each of secondary threads 116 is represented by a plurality of crests 120. The distance between every adjacent pair of crests 120 and 118 along a longitudinal axis 122 of dental implant 100, substantially equals to P/2. Secondary thread 116 ends with an intermediate screw turn 124, whose major diameter gradually reduces from $D_1$ to $D_3$. Alternatively, the major diameter of intermediate screw reduces from $D_1$ to $D_2$.

A jawbone (i.e., either the mandible or maxilla) of a human being includes a cortical bone below the gingiva, and a cancellous (spongy) bone below the cortical bone. The cortical bone is a substantially compact and solid bone, whereas the cancellous bone is porous and includes voids (similar to a sponge), and is not as strong as the cortical bone. Therefore, when a screw is tapped into the cortical bone and the cancellous bone of the jawbone, an upper portion of the screw which is located in the cortical bone, provides significant bonding that carries most of the load, while the lower portion of the screw which is located in the cancellous bone provides bonding of lesser significance.

The proof strength of a bolt which is tightened into a nut, in terms of tension and torque, is proportional to the stress area (i.e., the total surface area of those screw threads of the bolt which are in contact with the screw threads of the nut). Therefore, the greater the stress area, the greater the tensile load and the torque which the bolt can carry. The disclosed technique employs a screw whose coarsely threaded portion 112, which is located in the cancellous bone, has a stress area which is greater than that of finely threaded portion 110, which is located in the cortical bone. As the dental surgeon screws dental implant 100 into the jawbone, dental implant 100 compresses the cancellous bone surrounding the coarsely threaded portion of dental implant 100, thus strengthening the anchoring of dental implant 100 to the jawbone and expediting bone growth around dental implant 100. Therefore, the screw thread profile according to the disclosed technique provides a dental implant which has a proof strength substantially greater than that of a dental implant whose screw thread is uniform.

According to (1), minor diameter $D_2$ is smaller than minor diameter $D_3$. Therefore, the stress area of coarsely threaded portion 112 is greater than that of finely threaded portion 110. It is noted that the large thread height of primary thread 114 is larger than that of each of secondary threads 116. It is further noted, that since the pitch of primary thread 114 is substantially the same as that of each of secondary threads 116, after tapping a thread in the cortical bone by primary thread 114, each of secondary threads 116 carves and thus taps into a screw thread in parallel to the one formed by primary thread 114, in the cortical bone.

Dental implant 100 can include one or more longitudinal grooves (not shown), on a periphery thereof, disposed along longitudinal axis 122. Each of the longitudinal grooves can be located either on primary thread 114, each of secondary threads 116, or both primary thread 114 and secondary threads 116. While the dental surgeon screws dental implant 100 into the jawbone, bone particles which are produced due to the screwing action of primary thread 114 and secondary threads 116 into the jawbone, are deposited in the longitudinal grooves. In this manner, the longitudinal grooves serves as a depository for the bone particles. During the healing process, bone cells grow into the longitudinal grooves. Therefore, the longitudinal grooves provide an anchoring function in addition to that provided by primary thread 114 and secondary threads 116.

Figure 5D:
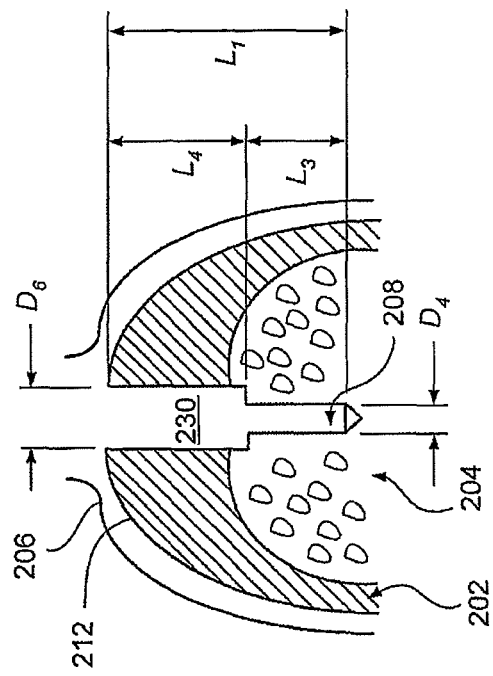
FIG. 5D is a schematic illustration of the mandible of FIG. 5A, ready for tapping therein the dental implant of FIG. 1.
Figure 5C:
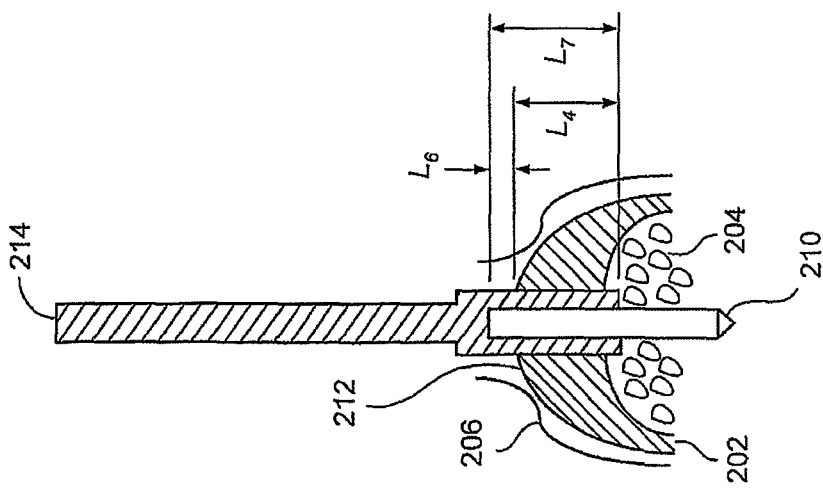
FIG. 5C is a schematic illustration of the mandible of FIG. 5B, in which another bore is drilled for tapping the secondary threads of the dental implant of FIG. 1, in a cortical bone of the mandible.
Figure 7:
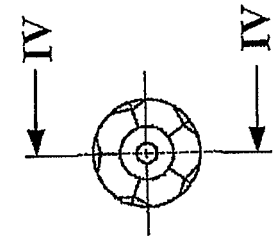
FIG. 7 is a schematic illustration of a side view (view III) of the drill bit of FIG. 6.
Figure 6:
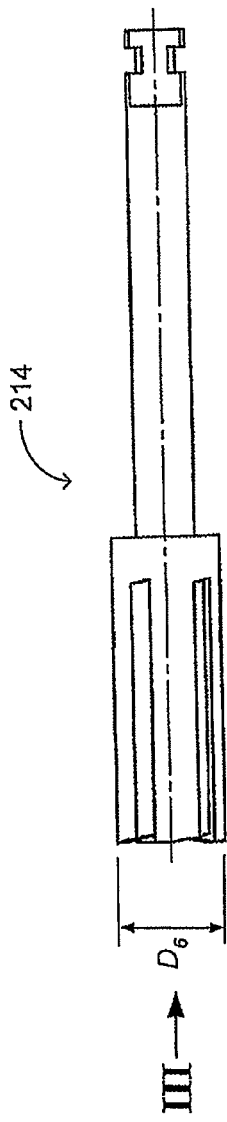
FIG. 6 is a schematic illustration of a drill bit employed for drilling the bore in the mandible of FIG. 5C, for tapping the secondary threads of FIG. 1, therein.
Figure 8:
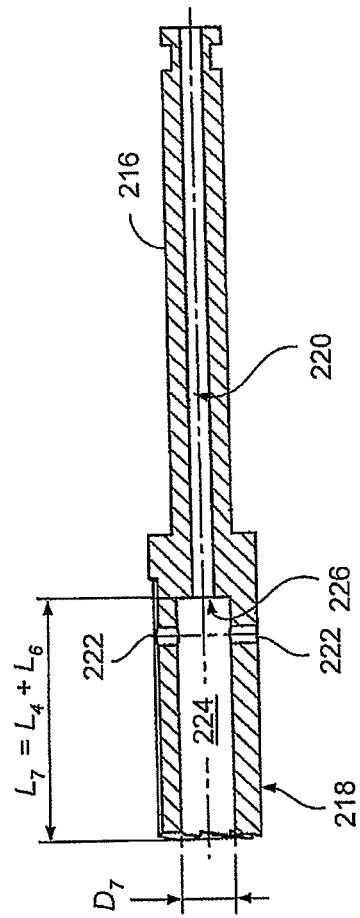
FIG. 8 is a schematic illustration of a section (section IV-IV) of the drill bit of FIG. 7.

Reference is now made to FIGS. 5A, 5B, 5C, 5D, 6, 7, and 8. FIG. 5A is a schematic illustration of a portion of a mandible in which a bore is drilled, for tapping the dental implant of FIG. 1, therein. FIG. 5B is a schematic illustration of the mandible of FIG. 5A, which includes a guide pin inserted into the bore illustrated in FIG. 5A. FIG. 5C is a schematic illustration of the mandible of FIG. 5B, in which another bore is drilled for tapping the secondary threads of the dental implant of FIG. 1, in a cortical bone of the mandible. FIG. 5D is a schematic illustration of the mandible of FIG. 5A, ready for tapping the dental implant of FIG. 1, therein. FIG. 6 is a schematic illustration of a drill bit employed for drilling the bore in the mandible of FIG. 5C, for tapping the secondary threads of FIG. 1, therein. FIG. 7 is a schematic illustration of a side view (view III) of the drill bit of FIG. 6. FIG. 8 is a schematic illustration of a section (section IV-IV) of the drill bit of FIG. 7.

With reference to FIG. 5A, a mandible 200 includes a cortical bone 202 and a cancellous bone 204. Cortical bone 202 is covered by a gingiva 206. A thickness of cortical bone 202 is designated by $L_4$. A bore 208, of a diameter $D_4$, is drilled to a depth $L_1$ (FIG. 1), from a crest line 212 into cortical bone 202 and cancellous bone 204.

With reference to FIG. 5B, a guide pin 210, of a length $L_5$, longer than the length $L_1$ (FIG. 1) of dental implant 100 (i.e., depth $L_1$ is the same as the length of dental implant 100), and a diameter $D_5$, is inserted into bore 208. Preferably, length $L_5$ of guide pin 210, is longer than $L_1$, by 3 mm. Diameter $D_5$ of guide pin 210 is equal to or greater than diameter $D_4$ (FIG. 5A) of bore 208. Guide pin 210 is made of a metal, such as stainless steel, titanium, and the like. Guide pin 210 protrudes from crest line 212 by a length $L_6$.

With reference to FIGS. 5C, 5D, 6, 7, and 8, a bore 230 of a diameter $D_6$, is drilled through cortical bone 202 and slightly penetrates cancellous bone 204, to a depth $L_4$ (FIG. 5D) from crest line 212, by employing a guided drill bit 214 (FIG. 6), while guide pin 210 is located within bore 208 (FIG. 5A). Depth $L_4$ is greater than the thickness of cortical bone 202. Considering the diversity of the thickness of cortical bone 202 among different patients, by selecting a typical value of 5 mm for $L_4$, total penetration of finely threaded portion 110 through all of cortical bone 202, as well as slight penetration into cancellous bone 204, is provided.

Guided drill bit 214 (FIG. 6) includes a shank 216 and a cutting portion 218. Shank 216 is employed for attaching guided drill bit 214 to a drill (not shown). Shank 216 includes an inlet cooling channel 220. Cutting portion 218 has a diameter $D_6$ (FIGS. 6 and 5D). Cutting portion 218 includes a plurality of outlet cooling holes 222 in a periphery thereof. Cutting portion 218 includes a bore 224 to fit guide pin 210 (FIG. 5B). Bore 224 has a diameter $D_7$ larger than $D_5$ (FIG. 5B) of guide pin 210. Bore 224 has a depth $L_7=L_4+L_6$.

While guide pin 210 is located within mandible 200, the dental surgeon uses guided drill bit 214 to drill bore 230 of diameter $D_6$ through cortical bone 202 into cancellous bone 204, by employing guide pin 210 as a pilot bit. When a bottom portion 226 (FIG. 8) of bore 224 makes contact with an end 228 (FIG. 5B) of guide pin 210, guided drill bit 214 ceases to advance any further into mandible 200. In this manner, bore 230 is drilled into cortical bone 202, to depth $L_4$ (FIG. 5C) from crest line 212. Inlet cooling channel 220 is in fluid communication with outlet cooling holes 222, in order to allow a cooling fluid to flow from inlet cooling channel 220 to hole 224, and out through outlet cooling holes 222.

With reference to FIG. 5D, after removing guide pin 210 and guided drill bit 214 from mandible 200, bore 230 of diameter $D_6$ to the depth of $L_4$ from crest line 212, is drilled through cortical bone 202, while slightly penetrating cancellous bone 204. The remainder of bore 208 is located within cancellous bone 204 from below cortical bone 202, having a depth $L_3$. The value of diameter $D_4$ (FIG. 5D) of bore 208 is selected according to the value of minor diameter $D_2$ (FIG. 3) of primary thread 114, such that primary thread 114 can be self tapped into bore 208 of cancellous bone 204. Similarly, the value of diameter $D_6$ of bore 230 is selected according to the value of minor diameter $D_3$ of each of secondary threads 116, in order to provide self tapping of each of secondary threads 116, into bore 230 of cortical bone 202.

The small thread height is substantially greater than the height of a micro thread, namely, substantially more than 0.2 mm. Preferably, the small thread height should be between 0.4 mm to 0.7 mm, and most preferably approximately 0.5 mm.

The values of the parameters of dental implant 100 can be for example, as follows:
$L_1$=13 mm
$L_2$=6.3 mm
$L_3$=6.7 mm
P=1.2 mm
α=45°
β=30°
$D_1$=4.5 mm
$D_2$=1.9 mm
$D_3$=3.5 mm
small thread height=0.5 mm (=$(D_1-D_3)/2$)
large thread height=0.5 mm (=$(D_i-D_2)/2$)

Figure 9:
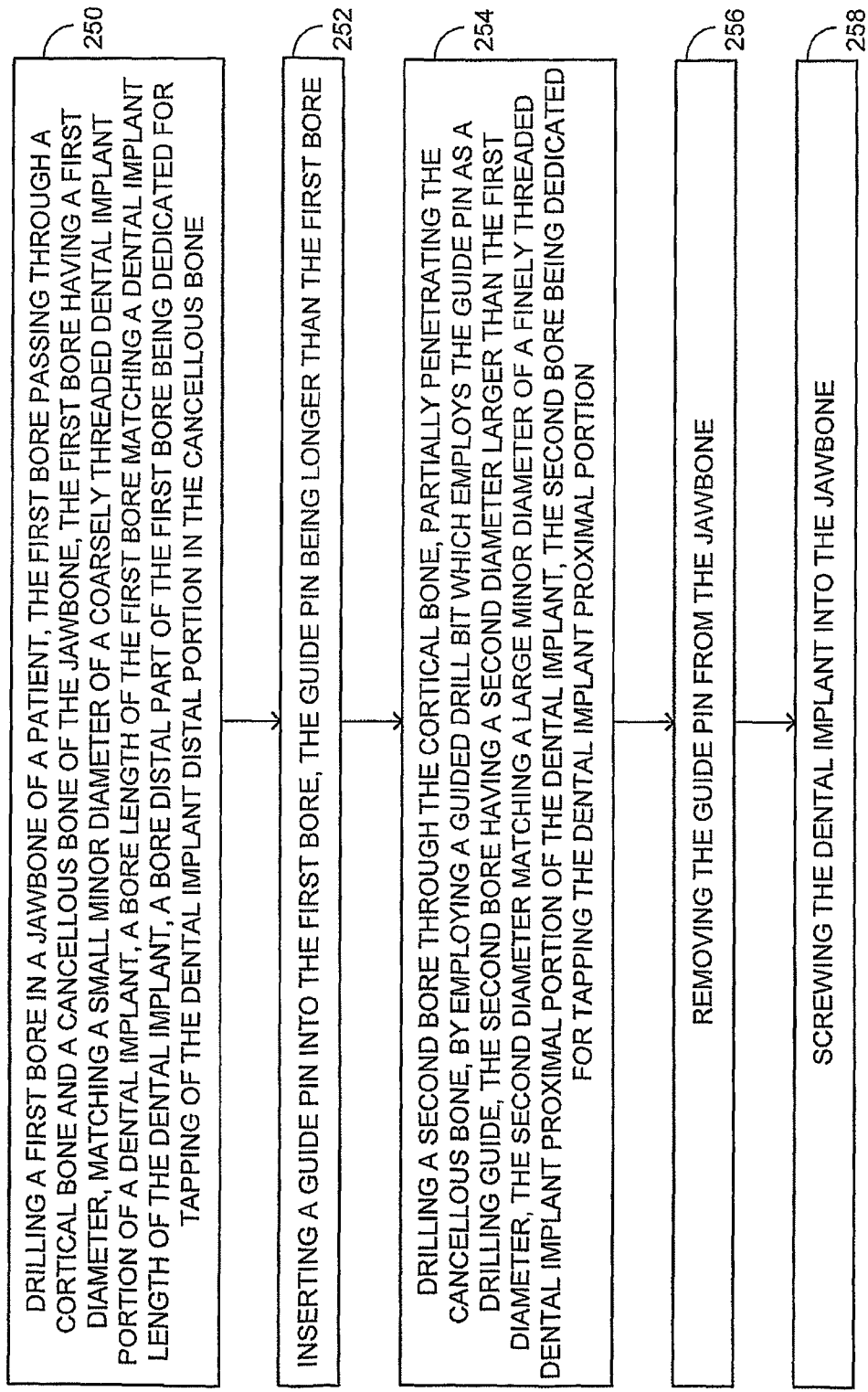
FIG. 9 is a schematic illustration of a method for implanting the dental implant of FIG. 1, into a jawbone of a patient, operative according to another embodiment of the disclosed technique.

Some of the parameters of dental implant 100 at proximal end 106 are for example, as follows:
$h_1$=0.4 mm
$h_2$=2.6 mm
$h_3$=3.7 mm
$h_4$=6.3 mm
$d_1$=1.3 mm
$d_2$=2.6 mm The values of the parameters of complementary drilling method and apparatus can be for example, as follows:
$D_4$=$D_5$=$D_2$=1.9 mm
$D_6$=3.5 mm
$D_7$=2.1 mm
$L_4$=$L_2$=6.3 mm
$L_5$=16 mm
$L_6$=3 mm
$L_7$=9.3 mm Reference is now made to FIG. 9, which is a schematic illustration of a method for implanting the dental implant of FIG. 1, into a jawbone of a patient, operative according to another embodiment of the disclosed technique. In procedure 250, a first bore is drilled in a jawbone of a patient, the first bore passing through a cortical bone and a cancellous bone of the jawbone. The first bore has a first diameter matching a small minor diameter of a coarsely threaded dental implant portion of a dental implant. A bore length of the first bore matches a dental implant length of the dental implant. A bore distal part of the first bore is dedicated for tapping of the dental implant distal portion into the cancellous bone.

With reference to FIGS. 1 and 5A, bore 208 of diameter $D_4$, is drilled into mandible 200. Bore 208 is drilled through both cortical bone 202 and cancellous bone 204.

In procedure 252, a guide pin is inserted into the first bore, the guide pin being longer than the first bore. With reference to FIG. 5B, guide pin 210 which is of a length $L_5$, longer than the length $L_1$ of dental implant 100 by a length $L_6$, is inserted into bore 208.

In procedure 254, a second bore is drilled through the cortical bone, partially penetrating the cancellous bone, by employing a guided drill bit which employs the guide pin as a drilling guide. The second bore has a second diameter larger than the first diameter. The second diameter matches a large minor diameter of a finely threaded dental implant proximal portion of the dental implant. The second bore is dedicated for tapping the dental implant proximal portion. With reference to FIGS. 1, 5C, and 5D, bore 230 of diameter $D_6$, is drilled through cortical bone 202 and into cancellous bone 204, by employing guided drill bit 214, which was inserted into mandible 200, in procedure 250. Guided drill bit 214 advances within cortical bone 202 and slightly further—into the cancellous bone 204 along guide pin 210, which is located within bore 224 of guided drill bit 214.

In procedure 256, the guide pin is removed from the jawbone. With reference to FIGS. 1 and 5D, the dental surgeon removes guide pin 210 from mandible 200, and implants dental implant 100 into mandible 200, by screwing of dental implant 100 into mandible 200 (procedure 258). Primary thread 114 taps a screw thread of pitch P in bore 230 of cortical bone 202. As dental implant 100 advances further into mandible 200, dental implant 100 taps one or more secondary threads 116, into bore 230 of cortical bone 202 while primary thread 114 is further advanced into the distal portion of bore 208 into cancellous bone 204. Since the pitch of each of secondary threads 116 is the same as that of primary thread 114, each of secondary threads 116 taps into a screw thread which is parallel to the screw thread tapped in cortical bone 202 by primary thread 114 in procedure 250. Further procedures in respect with the use of a mounting device, its application for screwing dental implant 100, removal of the mounting device, sealing of dental implant 100, and the coupling of an artificial tooth into dental implant 100, are described herein above in connection with FIGS. 1 to 3.

It will be appreciated by persons skilled in the art that the disclosed technique is not limited to what has been particularly shown and described hereinabove. Rather the scope of the disclosed technique is defined only by the claims, which follow.

The invention claimed is:

1. A dental implant for attaching therewith an artificial tooth to a jawbone, the dental implant comprising:
    a finely threaded portion configured for nesting within the entire width of a cortical bone of said jawbone and within a small portion of a cancellous bone of said jawbone, said finely threaded portion having a first number of thread crests per axial distance; and
    a coarsely threaded portion configured for nesting within said cancellous bone, said coarsely threaded portion having a second number of thread crests per axial distance, lesser than said first number of thread crests per axial distance,
    said dental implant including a plurality of primary threads running along both said finely threaded portion and said coarsely threaded portion, and one or more secondary threads running along said finely threaded portion at an offset from said primary threads, said offset is based on a number of said one or more secondary threads in said finely threaded portion,
    wherein the thread crests of the coarsely threaded portion are formed by said plurality of primary threads in the coarsely threaded portion, and the thread crests of the finely threaded portion are formed by the plurality of primary threads and the one or more secondary threads in the finely threaded portion,
    wherein the primary threads having a constant pitch and a constant major diameter throughout both said finely threaded portion and said coarsely threaded portion,
    said primary threads comprising a larger thread height in said coarsely threaded portion and a smaller thread height, lesser than said larger thread height, in said finely threaded portion,
    said primary threads comprising a larger minor diameter in said coarsely threaded portion and a smaller minor diameter, lesser than said larger minor diameter, in said finely threaded portion,
    wherein the secondary threads have constant pitch,
    wherein said smaller thread height is between 0.2 millimeter and 0.7 millimeter,
    wherein said larger thread height is between 1 and 1.4 millimeters,
    and wherein said constant major diameter is between 3.75 and 4.6 millimeters.

2. The dental implant according to claim 1, wherein said offset is based on P/(n+1), where "n" is equal to the number of said one or more secondary threads in said finely threaded portion, and "P" is the pitch of said primary threads.

3. The dental implant according to claim 1, wherein the value of said smaller thread height is between 0.4 and 0.7 millimeter.

4. The dental implant according to claim 3, wherein the value of said smaller thread height is 0.5 millimeter.

5. The dental implant according to claim 1, wherein the value of said larger thread height is 1.3 millimeters.

6. The dental implant according to claim 1, wherein said primary threads comprising a primary thread angle more acute than 45 degrees, and said secondary threads comprising a secondary thread angle more acute than 45 degrees.

7. The dental implant of claim 6, wherein the value of at least one of said primary thread angle and said secondary thread angle is 30 degrees.

8. The dental implant according to claim 1, wherein the value of said constant major diameter is 4.5 millimeters.

9. The dental implant according to claim 1, wherein the value of said constant pitch is between 1 and 1.3 millimeters.

10. The dental implant according to claim 1, wherein the value of said constant pitch is 1.2 millimeters.

11. The dental implant according to claim 1, wherein said finely threaded portion is between 5 to 6.5 millimeters long, and said coarsely threaded portion is between 6.5 to 8 millimeters long.

12. The dental implant according to claim 11, wherein said finely threaded portion is 6.3 millimeters long, and said coarsely threaded portion is 6.7 millimeters long.

13. The dental implant of claim 1, wherein a ratio between said larger thread height and said smaller thread height is between 2 to 2.5.

* * * * *